(12) United States Patent
Frandsen et al.

(10) Patent No.: US 6,297,505 B1
(45) Date of Patent: Oct. 2, 2001

(54) METHOD AND FLOW SYSTEM FOR SPECTROMETRY AND A CUVETTE FOR THE FLOW SYSTEM

(75) Inventors: Andreas Skærlund Frandsen, Slangerup; Søren Christian Pedersen, Hillerød; Carsten Ridder, Brønshøj; Henrik Thomsen, Hillerød, all of (DK)

(73) Assignee: Foss Electric A/S, Hillerod (DK)

( * ) Notice: Subject to any disclaimer, the term of this patent is extended or adjusted under 35 U.S.C. 154(b) by 0 days.

(21) Appl. No.: 09/297,331

(22) PCT Filed: Oct. 31, 1997

(86) PCT No.: PCT/DK97/00492

§ 371 Date: Apr. 30, 1999

§ 102(e) Date: Apr. 30, 1999

(87) PCT Pub. No.: WO98/20338

PCT Pub. Date: May 14, 1998

(30) Foreign Application Priority Data

Nov. 1, 1996 (DK) .................................................. 1221196

(51) Int. Cl.[7] .................................................. G01N 21/01
(52) U.S. Cl. ...................................... 250/339.12; 250/436
(58) Field of Search ................................ 250/339.12, 436

(56) References Cited

U.S. PATENT DOCUMENTS

| 3,781,116 | 12/1973 | Jones . |
| 3,886,364 | 5/1975 | Walker et al. . |
| 4,144,804 | 3/1979 | O'Keefe et al. . |

(List continued on next page.)

FOREIGN PATENT DOCUMENTS

| 4990/72 | 10/1971 | (DK) . |
| 4070/83 | 9/1982 | (DK) . |
| 0012492B1 | 6/1980 | (EP) . |

(List continued on next page.)

OTHER PUBLICATIONS

Christopher Scotter, Food Control, Jul. 1990, pp. 142–149, p. 146, right col., Line 24–p. 148.
Richard Streamer, PACE/Process and control engineering, vol. 39, No. 9, 1986 pp. 36, 38, 40, 42, 44, p. 30, middle col., lines 4–7, Figure 1.
Christopher Scotter, "Use of near infrared sepctroscopy in the food industry with particular reference to its applications to on/in–line food processes", Food Control, Jul. 1990.

(List continued on next page.)

Primary Examiner—Constantine Hannaher
Assistant Examiner—Andrew Israel

(57) ABSTRACT

The present invention relates to an on-line method and a flow system as well as a cuvette for carrying out IR spectrometry for analysis of liquid food products, possibly containing dissolved gases, in a process line in a liquid food product processing plant, especially a dairy processing milk and milk products. A liquid sample is extracted from the process line to a measuring branch, the sample is thermostated and passed to a measurement cuvette. The IR-absorbance spectrum is measured, e.g. in the MID-IR or NIR-range. In order to obtain an on-line monitoring of the process line the liquid food sample is extracted directly from the process line into the measurement branch, in which the pressure is maintaining at least as high as in the adjacent process line. The high pressure ensures that dissolved air will stay dissolved in the liquid food. Before each new sample the measurement branch and cuvette are flushed by high flow rates with a part of the new sample to clean the cuvette. The measurement cuvette has strong windows, preferably diamond windows to stand a high pressure and high flow rates. The on-line system is arranged to carry out eg. 120 measurements per hour.

33 Claims, 7 Drawing Sheets

U.S. PATENT DOCUMENTS

| | | |
|---|---|---|
| 4,239,394 | 12/1980 | Aegidius et al. . |
| 4,910,403 | 3/1990 | Kilham et al. . |
| 5,003,174 | 3/1991 | Datwyler et al. . |
| 5,046,854 | 9/1991 | Weller et al. . |
| 5,137,738 | 8/1992 | Wynn . |
| 5,452,232 | 9/1995 | Espinosa et al. . |

FOREIGN PATENT DOCUMENTS

| | | |
|---|---|---|
| 0629290B1 | 12/1994 | (EP) . |
| 1305214 | 1/1973 | (GB) . |
| 2028498A | 3/1980 | (GB) . |
| 2028498B | 3/1980 | (GB) . |
| 2104681A | 3/1983 | (GB) . |
| 404844 | 10/1978 | (SE) . |
| 95/07461 | 3/1995 | (WO) . |

OTHER PUBLICATIONS

Richard Streamer, "On–line near IR analysis", Pace/Progress and Controll Engineering, vol. 39, No. 9, pp. 40–44, 1986.

Peter R. Griffiths et al., "Fourier Transform Infrared Spectrometry," John Wiley & Sons, 1986, pp. 144–145.

METHOD AND FLOW SYSTEM FOR SPECTROMETRY AND A CUVETTE FOR THE FLOW SYSTEM

This application is the national phase under 35 U.S.C. §371 of PCT International Application No. PCT/DK97/00492 which has an International filing date of Oct. 31, 1997 which designated the United States of America.

TECHNICAL FIELD

The present invention relates to a method and a flow system for carrying out spectrometry for analysis of a liquid food product, possibly containing dissolved gases, in a process line in a liquid food product processing plant, especially milk and milk products in a dairy, and comprising the following steps: 1) providing a liquid food sample from the process line to a measuring branch, 2) thermostating the liquid food sample, 3) passing the thermostated liquid food sample to a sample cuvette, 4) measuring at least part of the absorbance spectrum of the liquid food sample in the sample cuvette. The invention also relates to a measurement cuvette for the flow system. The present invention is specifically intended for IR-measurements, e.g. MID-IR and/or NIR-measurements for a determination of the quantities of specified components in the liquid food product.

BACKGROUND ART

A presently used method includes providing a milk sample from the process plant in an open sample container or cup from which dissolved gases may escape, passing part of the degassed milk sample from the container through a measurement branch into a measurement cuvette, performing the test and passing the tested milk sample to a waste outlet.

The presently used test instrument includes generally a flow system, an IR spectrophotometer, and a computer comprising a PC with hard-disc, floppy disc drive, monitor and keyboard.

Instead of the above mentioned method it would be preferable to perform the test on-line and in-line in the process plant, and preferably in such a way that it also would be possible to let the tested milk sample be returned into the process line, to avoid the waste.

U.S. Pat. No. 5,137,738 discloses a system and a method for controlling the butterfat content of milk. The entire product stream is monitored continuously by the use of optical density sensors. The preferred sensors have stainless steel bodies and housings med Pyrex windows and mount directly on the product output lines and operate at full flow and pressure. U.S. Pat. No. 4,144,804 discloses a photoelectric monitoring system for continuously measuring the butterfat content of a sample of homogenized milk as the latter flows continuously through the processing system under the pressure of the homogenizer in the system. The known on-line sensors for milk products do not apply spectrometric analysis of the content. On-line spectrum measurement for determining a property of a product is known, e.g. as described in U.S. Pat. No. 5,452,232 for a hydrocarbon product. GB-A-2 104 681 describes an apparatus for the continuous investigation of chemical reactions by infrared absorption by use of an IR spectrophotometer having a through flow cell through which flows a continuous sample stream branched off from the reaction container. U.S. Pat. No. 4,910,403 describes a flow cell utilized on-line in the analysis of molten polymer. The flow cell includes diamond windows for passing mid to far infrared radiation through the molten polymer flowing through the flow cell.

Testing milk in-line in a process plant in a dairy presents several problems. One problem is due to dissolved air, which is normally present in the raw milk. If air bubbles are released and enter the measuring cuvette, the measurement result will obviously not show a correct analysis of the milk product itself. A further problem is that milk includes several components and specifically the fat globules can give reason to failures. According to the known art the temperature of the milk sample should be raised to about 35–42° C., and preferably homogenized to make reliable, reproducible measurements possible in an IR cuvette. Obviously, the milk in the process plant is generally kept at a low temperature to avoid the milk to be spoiled by some unwanted reactions, such as growing bacteria's.

A further problem is that thin layers of milk tend to adhere to the IR-windows of the cuvette. The measurements may be seriously deteriorated due to such milk coatings. Therefore, an IR cuvette needs regular thorough cleaning.

An in-line and on-line system must be able to measure reliably and normally without needing any regular calibrations and adjusting. Spectrometric measurements require the utmost stability of the components of the optical system. It is very important that the cuvette is extremely stable and not liable to suffer from wear. In fact the cuvette is highly exposed to wear as the liquid product and rinsing and cleaning solutions pass through the cuvette under high pressure and flow rates.

It has therefore until now not been possible to perform the desired testing procedures on milk in an in-line system. To the applicants best knowledge there does not on the market exist any reliable apparatus able to perform accurate and reliable in-line determinations of the quantities of the components in raw milk or in a milk product, e.g. fat, protein, lactose, urea and casein.

SUMMARY OF THE INVENTION

According to the invention the method as defined in the preamble comprises extracting the liquid food sample directly from the process line into the measuring branch, providing and maintaining a pressure that is at least as high as the pressure in the said process line, and before each measurement flushing the cuvette with part of the recently (latest) extracted liquid food sample, further having provided that the cuvette having windows of a pressure and wear resistant material, being especially resistant to mechanical and chemical influences of the kind appearing in dairies. The flushing is performed under a pressure of from 100–200 bars, preferably from 110–150 bars across the cuvette, so the flushing rate will be high enough to ensure a thorough removal of the old sample including a cleaning of the cuvette.

The high pressure ensures that dissolved air will stay dissolved in the liquid food. The pressure and wear resistant materials, preferably diamond windows, allow the cuvette to stand high pressures and high flow rates. Other window materials might break or move causing the cuvette to widen and to thereby causing the IR transmission loss through the cuvette to raise, thereby influencing the measurement result. Accordingly the pressure in the measurement branch should preferably be kept high, at least as high as the pressure in the process line at the location on which the sample is extracted, and during measurements the pressure shall be kept constant in the cuvette. Preferably, the pressure in the measuring branch exceeds the pressure in the process plant to ensure that dissolved air stays dissolved in the liquid food.

The method is specifically fitted for liquid food products such as raw milk or processed milk and other dairy products.

In one embodiment the measuring branch forms a closed system together with the process line. This means that the measuring branch only receives liquids flowing in the process conduit to which the measuring branch is connected.

Preferably, a regular (e.g. daily) cleaning of the measuring branch including the cuvette is performed when the dairy plant is subjected to the regular cleaning process and/or by flushing the branch with the same cleaning solutions used for cleaning the dairy plant. In an advantageous embodiment of the present invention at least one of the cleaning or rinsing liquids of the dairy may be used in the measuring branch for an adjustment, such as a standardization based on characteristics in the measured spectrum or spectra of the cleaning or rinsing liquids, especially characteristics originating from the appearance of ions belonging to the group comprising $NO_3^-$-ions and $PO_4^{3-}$. (By "standardization" is meant an adjustment of the instrument, (e.g. performed in the instrument software) made in order to make a plurality of spectrum measuring instruments performing in the same way so that copies of the same calibration software can be used on all the instruments and whereby all instruments will provide the same result when measuring the same sample.)

Preferably, the spectrometry is performed in the IR spectral range, e.g. in the MID-IR and/or the NIR spectral range, these ranges being specifically favourable for the analysis of milk.

In an advantageous method the liquid food sample is thermostated while it is maintained inside the cylinder of a single stroke pump whereby a separate preheater possibly can be dispensed with. A homogenizer may be included in the measuring branch. A thorough homogenization is preferred in order to obtain a representative sample inside the very thin cuvette. If the measurement system is located at a position in a dairy where the milk product passing the sample intake always is adequately homogenized, a further homogenizing can be deleted, and the measurement branch may be set up without homogenizer. As it will appear clearly from the detailed description the method according to the invention allow about 120 on-line IR spectrometry measurements per hour.

The present invention further provides a flow system for extraction of a sample stream from a liquid food processing plant such as a dairy processing milk and milk products, and for carrying out the method according to claim 1. According to the invention the flow system is directly connected to the liquid food processing plant, the flow system including a measurement cuvette for spectrometric measurements for determination of the quantities of the known components in a liquid food product in a liquid food processing plant, and the flow system comprises pump means and back pressure valve means to maintain a predetermined pressure inside the cuvette, said pressure being at least as high as the pressure in the process plant, and the cuvette having windows of a material, which is resistant to pressure and wear and especially to mechanical and chemical influences of the kind appearing in a diary. Preferably, the measurement cuvette has diamond windows, as diamond is an extremely wear and pressure resistant material.

Preferably the liquid food sample is extracted from the process line by a pump providing a high flow rate in the measuring branch, said flow rate inside the cuvette at least for a short period exceeding 5 m/s, preferably exceeding 20 m/s and more preferably reaching about 25-30 m/s, to flush the measuring branch and specifically the cuvette to avoid the building up of a coating of liquid food on the IR-windows. In a preferred embodiment the pump means is a single stroke pump. The single stroke pump is specifically advantageous in that the suction stroke can be slow in order to avoid cavitation when sucking in a new sample, still allowing a fast pump stroke in order to provide the high flow rate of the sample when the cuvette is flushed with a new sample in order to remove all rests or remnants from the former sample.

The present invention further provides a measurement cuvette for a flow system according to claim 7, the cuvette comprising: a first and a second steel member enclosing an IR measurement chamber between two IR windows, the first steel member having boreholes for inlet and outlet of a liquid flow to and from the IR measurement chamber, one of the steel members having an opening for arrangement of an optical detector, the other member having an opening provided for an IR-light beam coming from an IR-source, each opening being sealingly dosed by a diamond disc, forming one of the windows, and the two steel members with diamond windows being tightly secured to each other by fastening means. Thereby a stable, wear resistant cuvette is provided. This cuvette is well fitted for a flow system and measurement system wherein regular calibrations and adjustments can be dispensed with. spacer_being tightly secured to each other by fastening means. Thereby a stable, wear resistant cuvette is provided. This cuvette is well fitted for a flow system and measurement system wherein regular calibrations and adjustments can be dispensed with. The spacer defines the correct distance (path length) between the windows. The spacer supports and stabilizes the windows, when the chamber is flushed and filled with the liquid food. Preferably the opening in the spacer defining the light penetrating part of the windows has a diameter of less than 2.5 mm and preferably about 2 mm. It is preferred to have small windows because this will reduce the deflection when the chamber is exposed to high pressures. In an advantageous embodiment the spacer has a wedge form providing a change in width/height of spacer (equal to light path in chamber) of about 3–10 $\mu$m, e.g. about 6 $\mu$m across the 2 mm opening. Such wedge form will reduce or eliminate the tendency to the occurrence of internal reflections of the light beam inside the chamber.

Utility of the Invention

The improved method and the measurement cell therefore are intended for use in liquid food processing plants and more specifically dairies. In the following description the term milk includes raw milk and food products derived from that, and may include other kinds of liquid food products.

Advantages Obtained by the Invention:

The measurement takes place at normal process line pressure or even higher. Therefore, dissolved gases will not be released and accordingly, no air bubbles are produced. The measuring system is chemical resistant to all substances which stainless steel is resistant to. (This feature is an advantage during a regular cleaning of the food product processing system). The diamond windows ensure that the mechanical dimensions of the optical system are not subject to changes due to mechanical wear. The measuring system can operate in a process environment for a long time without any need for attended operators to perform zero adjustment, re-calibration, separate cleaning or other kind of maintenance operation on the flow system and IR measurement equipment. The measurement is an on-line measurement, always available to maintain an optimal production. Regularly, during normal operation, the flow system is "cleaned" by the samples themselves. Preferably, in a preferred embodiment, the normal process line cleaning procedure includes the measuring branch, i.e. the above mentioned flow system. Further, in the preferred embodiments, no "foreign" substances are introduced, i.e. no special cleaning or calibration agents are needed besides the cleaning and rinsing agents generally used in dairies. Therefore, a possible option comprises the return of the sample to the process line after the measurement.

DETAILED DESCRIPTION OF THE BEST MODE FOR CARRYING OUT THE INVENTION

A preferred embodiment of a system for carrying out the method according to the invention comprises the following major components: A flow system 100, an optical MID-IR spectrometry system 200 and a control system 300 as indicated in FIG. 1.

Figure 1:
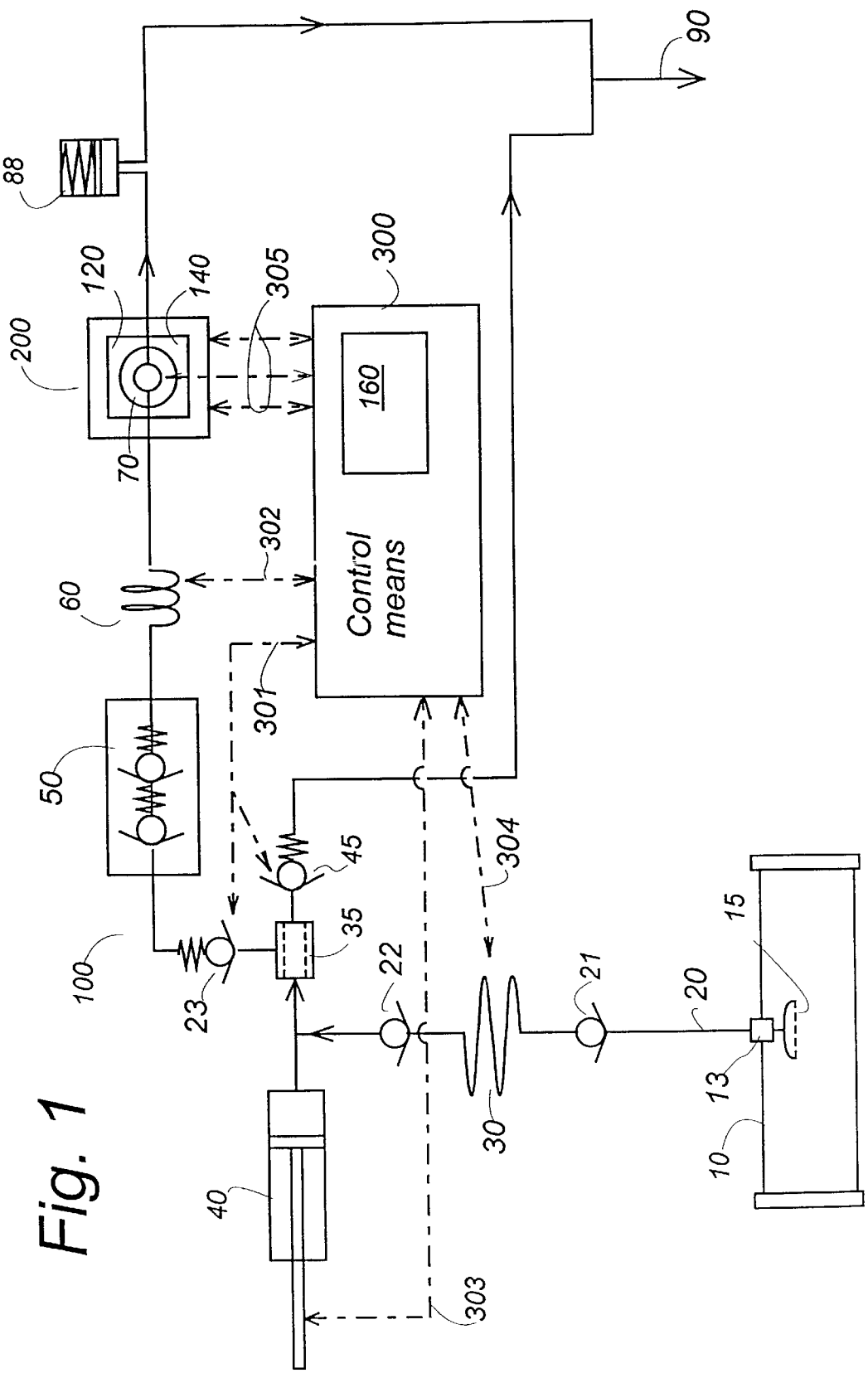
FIG. 1 is a schematic diagram of an example of a measurement system and flow system according to the present invention.
Figure 2:
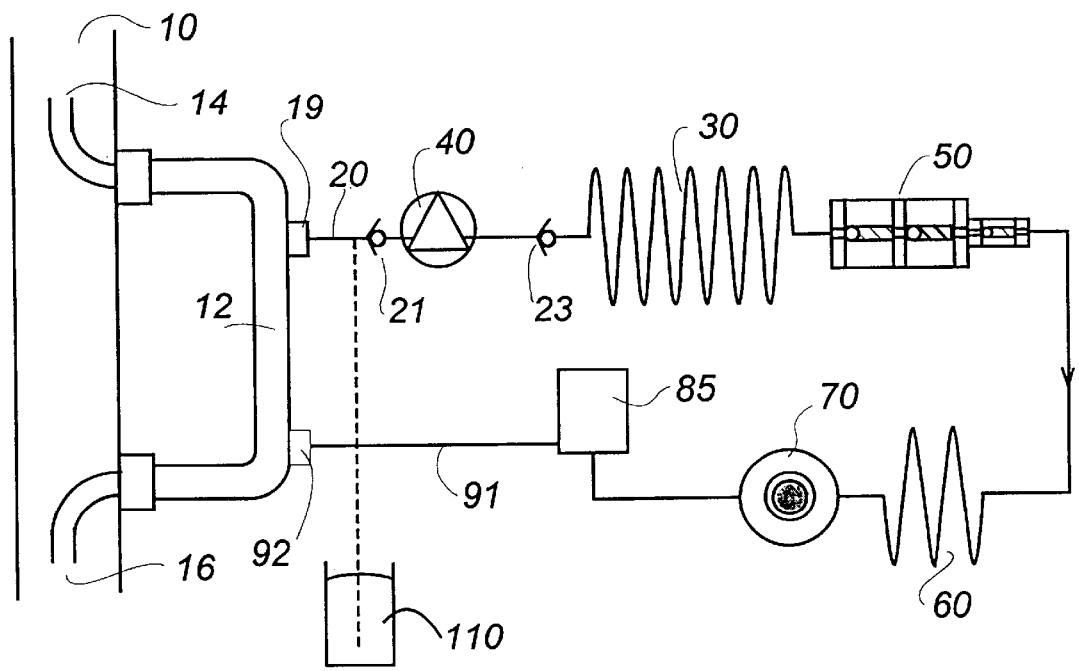
FIG. 2 is a schematic diagram of an example of a modified flow system according to the present invention.
Figure 3:
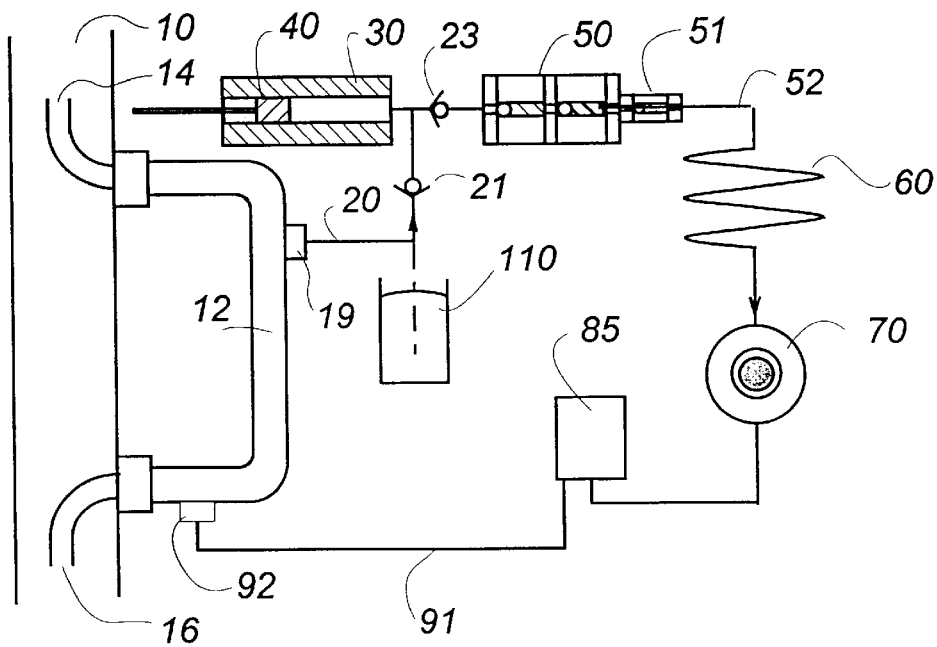
FIG. 3 is a schematic diagram of a third example of a flow system according to the present invention.

The flow system may comprise the following components as shown in the three examples FIG. 1–3.

Sample intake means, comprising a tube 20 and a pump and valve means, e.g. a piston pump 40 having at least one one-way valve 21, 22 at the pump inlet and at least one one-way valve 23, 45 at the pump outlet. The sample intake means 20 is connected to a section of a process conduit 10 from which the samples are taken through a filter 15 and through a detachable connection e.g. mini clamps 13 comprising two flange parts and a gasket. Preferably all such connections are made according to the hygienic standards for food processing plants. The process conduit 10 is part of a food processing plant such as a dairy, which is not shown.

Thermostatizing means 30, preferably comprising: a preheater or cooler, e.g., a coiled steel tube embedded in or wound around an electrically heated copper cylinder, providing e.g. from 1 to 5 ml, preferably 1.5 ml of heated milk or a heated copper cylinder having an inner volume of about 15 ml and assigned temperature sensing means (not shown) connected to control means 300 for controlling the preheater or cooler. The heating means 30 are designed to heat e.g. 1.5 ml milk from 1° C. to a temperature about 40° C.–50° C. in about 25 seconds.

A high pressure pump 40, (e.g. a LPA/MSC50h-pump as used in a FOSS ELECTRIC MILKOSCAN 50 or a single stroke pump providing a whole sample volume—e.g. 1.5 ml in one single stroke) provides the high pressure (e.g. about 400–500 bar). Typically at least a pressure of 200 bars is needed for homogenizing. Further the pump yield 40 will ensure a high flow rate through the IR-cuvette during a flushing period, so that the cuvette is cleaned by means of the flow rate of the milk, making further cleaning unnecessary for a number of hours. During the flushing period the pressure across the cuvette may reach 100–200 bars. To avoid degassing in the measurement period, the pressure of the measuring branch is maintained at at least the same pressure as the pressure at the location on which the sample is extracted from the process plant Preferably the pressure in the measuring branch exceeds the pressure in the process plant During a measurement the pressure is maintained at a substantially constant level by the use of a back pressure valve 88 as explained later.

In the embodiment shown in FIG. 1 an in-line filter 35 provides a filtered milk passing through the measurement branch comprising the cuvette 70. Optionally a valve 45 (FIG. 1) allows the milk to bypass the filter, the milk running directly towards waste 90. The high flow rate of milk along the inside of the filter 35 will provide a cleaning of the filter 35 when the valve 45 is open. To this end the valve 45 can be controlled by the control means 300. Preferably, the valve 45 also act as a safety valve which is set to open if the pressure exceeds e.g. 400 bars.

A homogenizer 50 (e.g. a S4000 as used in FOSS ELECTRIC MILKOSCAN 4000). A thorough homogenization of the liquid food product is needed in order to obtain a representative sample (a sample containing all components in the liquid food product) inside the very thin cuvette (typically having a width of 37–50 $\mu$m). A further reason for including homogenization is that the scattering of the infra red light passing through the cuvette depends on the particle size of the liquid sample. Accordingly a uniform homogenization is essential in order to have reproducible measurement conditions. The pressure drop across the homogenizer is about 200 bars. In the embodiments shown in FIG. 2 and 3 a safety valve also functioning as a contra valve 51 follows immediately after the homogenizer.

A further preheater or cooler 60, e.g. a coiled tube preferably wound on the periphery of a temperature stabilised IR cuvette, having an electrical resistor soldered to a copper body thermostatizing the milk sample to a predetermined temperature, e.g. to about 40° C. and preferably to 50° C. before entering the cuvette, and preferably comprising assigned temperature sensoring means connected to the control means 300 for controlling the temperature of the preheater or cooler. These controls and assignments are illustrated by phantom lines in FIG. 1.

Figure 6A:
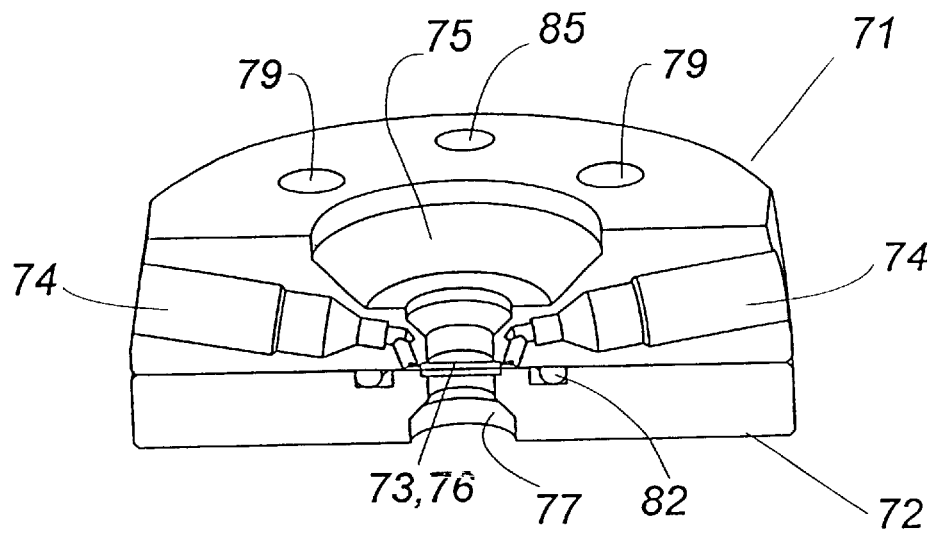
FIG. 6A is an oblique sectional view of a preferred embodiment of an IR cuvette according to the present invention, seen from above and in an enlarged scale.
Figure 6B:
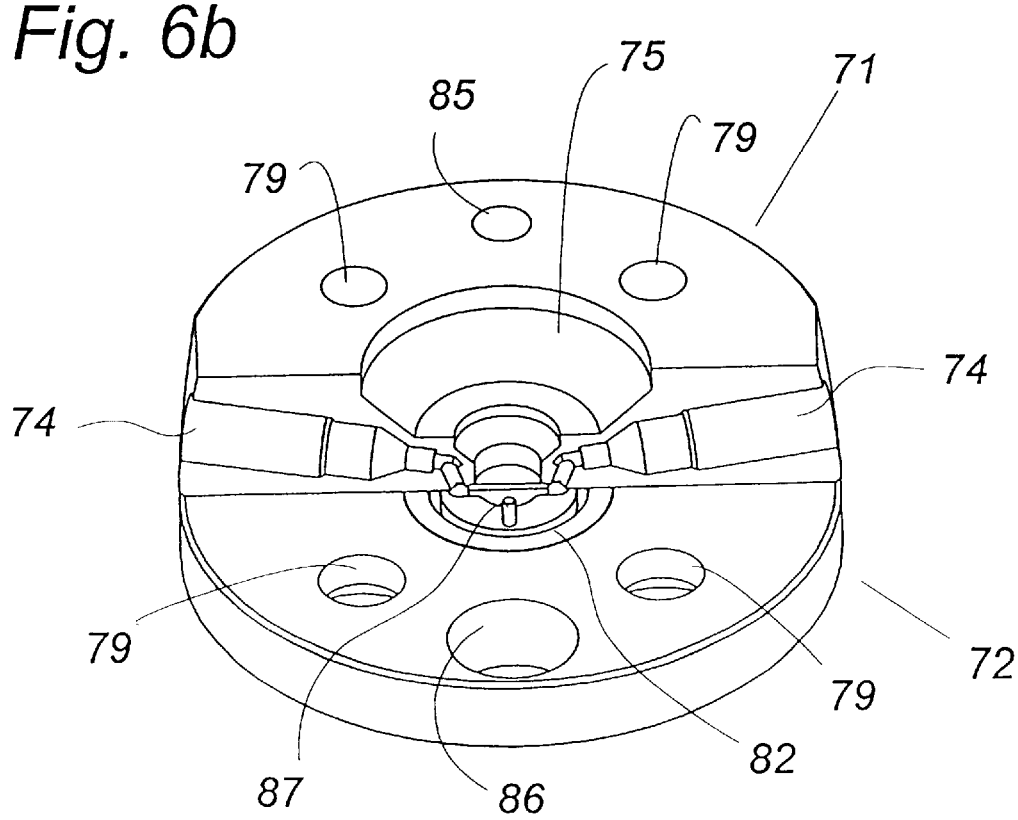
FIG. 6B same as FIG. 6A, also showing the front half of the lower part.
Figure 7:
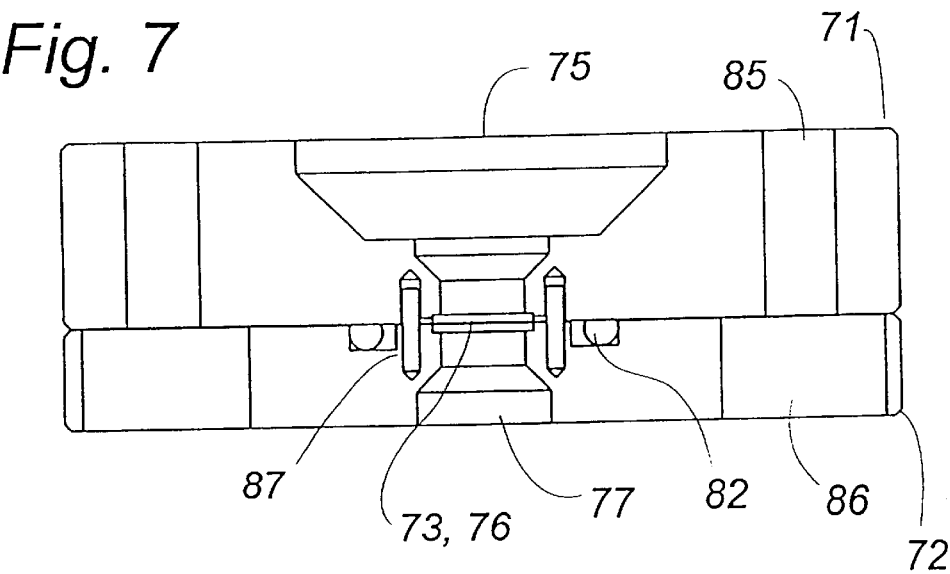
FIG. 7 is a sectional view along line C—C in FIG. 8 of the embodiment shown in FIG. 6A and B in an enlarged scale.
Figure 8:
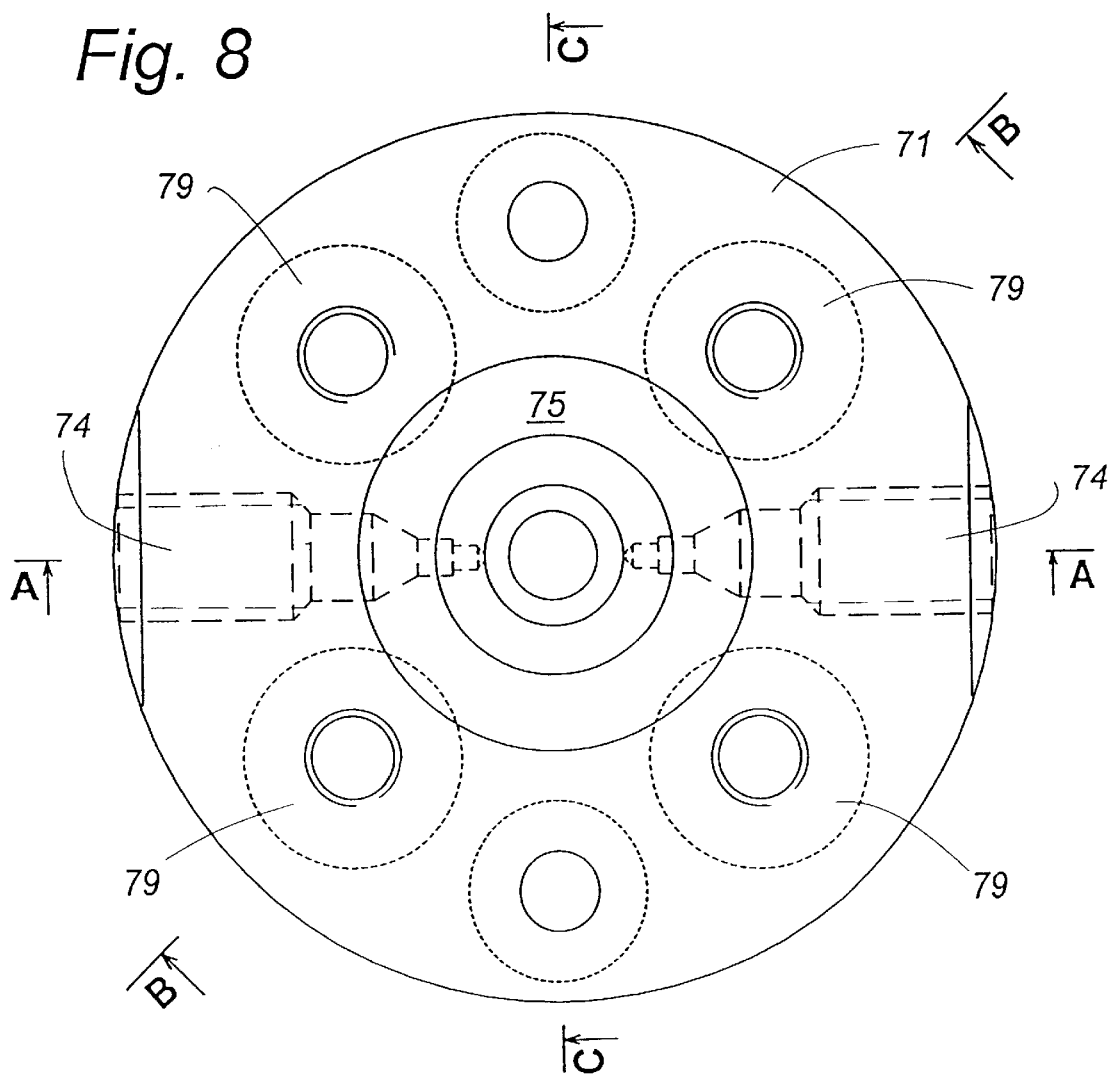
FIG. 8 a schematic top view of an IR cuvette in an enlarged scale.

An IR cuvette 70, comprising a milk flow path and an IR light path crossing the milk flow path. The IR cuvette is part of an IR spectro-photo-meter allowing the analysis and/or quantitative determination of specific components of the milk in the JR cuvette. Preferably the IR cuvette structure induces a bypass milk flow path 83 (FIG. 9) for the auxiliary milk, which is unable to pass through the very thin measurement chamber in the IR cuvette; A presently preferred embodiment of the cuvette 70 is shown in FIG. 6–8 and described in detail later in this specification.

A back pressure valve 88 maintains a predetermined pressure at the cuvette 70 during the measurement, typically 12 bars, and at least as high as the pressure in the process conduit 10. This pressure will ensure that dissolved gases remain dissolved in the milk in order to avoid air bubbles in the cuvette. Further, in stationary periods (i.e. no flow) the back pressure valve will ensure that the pressure do not exceed 12 bars A substantially constant pressure in the cuvette is necessary to obtain reliable and reproducible spectrometric measurements.

An outlet 90 for waste and means (not shown) for collecting or evacuating the waste. Optionally the sample may be returned to the milk processing plant. This possibility is available because no foreign means or agents have been added to the sample.

In a second embodiment shown in FIG. 2 the flow system comprises: a fast-loop, i.e. an U-formed tube 12 having an inlet 14 and an outlet 16 arranged inside a process conduit 10 which is part of a process plant such as a dairy, which is not shown in the drawings. The is fast-loop tube 12 is small compared to the process conduit 10. Typically the inner diameter of the fast loop is about 10 mm in a process conduit 10 having an inner diameter of about 70 mm. The drawing does not show the true dimensions.

The inlet 14 opens towards the direction of the process flow in the conduit 10, in such a way that a fraction of the process flow is diverted through the fast-loop. At the outlet 16 the process flow will generate suction, forcing the diverted flow to return into the process conduit 10.

A sample intake is provided by a tiny flexible tube 20, having an inlet opening with filter communicating with the fast-loop through a detachable connection e.g. so-called mini clamps 19 comprising two flange parts and a gasket Preferably all such connections are made according to the hygienic standards for food processing plants. Similar to the system in FIG. 1 a pump 40 transfers the sample to a preheater 30, followed by a homogeniser 50, a further preheater 60, an IR-cuvette 70 and a back pressure valve 88. The sample may be returned to the fast-loop through a further tiny tube 91, e.g. a plastic tube or hose. Alternatively it may be released as waste.

In a third preferred embodiment shown in FIG. 3 the flow system comprises a fast loop 12, connected to a process conduit 10. An integrated unit comprising a single stroke pump 40, surrounded by a heater, e.g. a heating coil, forming the first preheater 30, and two one way valves 21, 23 providing that the single stroke pump during a suction stroke takes in milk from the fast loop, and during the pressure stroke sends the milk directly into the homogeniser 50. The homogeniser 50 is at the outlet provided with a valve 51 acting as a safety valve or pressure release valve, in order to release an extraordinary high pressure which otherwise might destroy the cuvette. A tiny tube 52 carries the homogenised milk to a further preheater 60, the cuvette 70 and the back pressure valve 88 in the same way as in the other embodiments. In a modification of the embodiments shown in FIG. 1–3 the one way valve 23 is deleted as the one way function is inherently incorporated in the preferred homogenizer 50.

The Optical System

The optical system 200 for measuring the IR absorption, preferably the MID-IR absorption, can be chosen between several known MID-IR spectrometric systems, and realised in several ways. Preferably a scanning interferometer, i.e. a FT-IR instrument is used, e.g. an IR-unit as used in FOSS ELECTRIC MILKOSCAN 120. However, the optical system may instead include a filter wheel, comprising a plurality of IR filters appropriate for the desired measurements, e.g. as used in a FOSS ELECTRIC MILKOSCAN 50 or MILKOSCAN 102–104 and as described in GB-B-2 028 498, EP 0 012 492 and EP 0 629 290.

Figure 4:
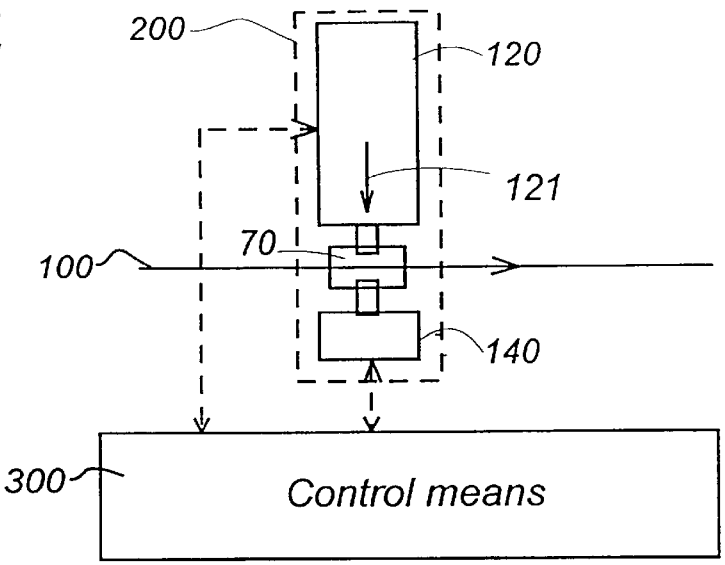
FIG. 4 is a schematic diagram of an optical system in a measurement system according to the present invention.

A simplified diagram of a suitable optical arrangement appears from FIG. 1 and FIG. 4. The Box 120 is an IR-source and scanning interferometer, 140 is a detector, and 160 is a computer. Scanning interferometers can be realised in several ways, cf., e.g. "Fourier Transform Infrared Spectrometry", Peter R. Griffiths and James A de Haseth, John Wiley & Sons, 1986, and shall not be the topic of this application. The calculations for the determination of the quantities of the components in the milk are performed in the computer 160, and they are also well known to people in the art, e.g. as described in the above reference.

The IR Cuvette

In the following the IR cuvette is described in detail. The IR-cuvette is designed for an optical path length of e.g. 37–50 μm. The IR-cuvette must be made of strong materials, which are resistant to wear and pressure and resistant to mechanical and chemical influences, e.g. materials as used for the process plant itself. Preferably the IR cuvette is made from a stainless steel and diamond. Accordingly, the IR cuvette can be cleaned by the same liquid means which are used for the milk processing plant anyway in the dairy. Milk processing plants in dairies are regularly, e.g. daily/every 24 hours, flushed with several cleaning liquids, e.g. strong bases and/or acids.

The diamond and steel materials ensure that the cuvette will not be subjected to any noticeable wear.

The physical dimensions and properties of the IR light path should be kept constant, preferably for the whole lifetime of the cuvette. Only the milk sample to be tested is changing. This is extremely important to the accuracy and reproducibility of the IR measurements.

Figure 5A:
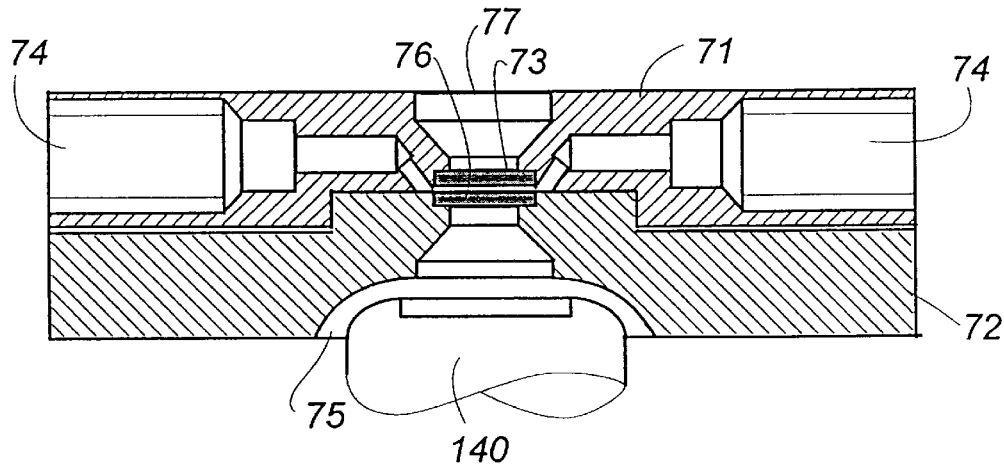
FIG. 5A is a schematic sectional view along line A—A in FIG. 8 of an example of an embodiment of an IR cuvette according to the invention and in an enlarged scale.
Figure 5B:
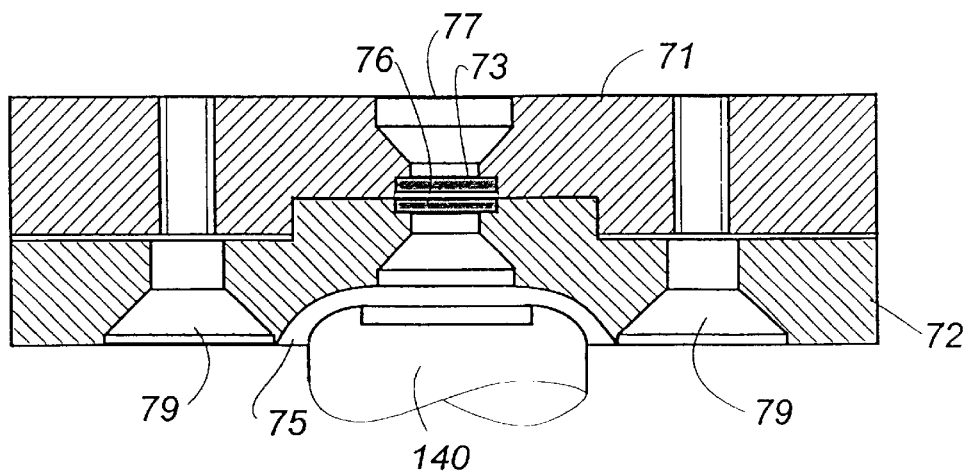
FIG. 5B same along line EBB in FIG. 8.

An enlarged view of a first example of an embodiment of a cuvette is shown is FIG. 5A and FIG. 5B. An alternative embodiment of the IR cuvette is shown as a second example in FIGS. 6A, 6B, and 7. FIG. 8 is a schematic top view which applies to both examples. Therefore the sections applied in FIGS. 5A, 5B are shown on the schematic FIG. 8 as well as the section C—C applied in FIG. 7. In both embodiments the cuvette comprises two steel members 71, 72, e.g. two circular discs. The first steel member 71 has a recess for mounting a diamond window 73, and two stepped boreholes 74 (flow channels) for the milk flow. The second steel member 72 has a recess for mounting a second diamond window 76. The two steel members 71, 72 are tightly secured to each other by fastening means, e.g. four recessed screws (not shown) in threaded bores 79.

As shown in the embodiment of FIG. 5A, 5B one of the steel members 71 may have a recessed central area in which a protruding portion 69 of the other steel member 72 can intrude or visa versa.

As shown in FIG. 5A the cuvette is preferably connected in the flow system by tiny tubes 78 which are inserted in each borehole 74. For the sake of clarity only one tube 78 is shown.

In the embodiment of FIG. 5A, 5B the first steel member 71 has an upper stepped opening 77 provided for an IR light beam 121 from the optical system 200 in FIG. 4, and the second steel member 72 has a lower stepped opening 75 provided for a detector 140 in the optical system. An alternative arrangement is shown in the embodiment of FIGS. 6A, 6B and 7. In FIGS. 6A, 6B and 7 the first steel member 71 has the stepped opening 75 provided for the detector 140 in the optical system, and the second steel member 72 has the stepped opening 77 provided for an IR light beam 121 from the optical system.

When designing the cuvette enclosing the very thin measurement chamber between the two diamond windows it was found appropriate to design the cuvette so that the milk sample is let in through a first bore hole 74, which is made from the outer periphery of the cuvette, and a second bore hole 84, which is made from that side of the steel member, which will abut the second steel member when they are assembled. Therefore, the two bore holes form a mutual angle of about 100°–140°, preferably 120°–125°. Further it may be an advantage to let the bore hole 74 be inclined to form an angle α (not shown in the drawings) with the interface between the two steel members 71, 72, where α is between 0° and 30°, preferably between 5° and 15°, and most preferably about 10°. The adjacent bore (84 in FIG. 9) forms an angle β (not shown in the drawings) with the interface between the two steel members 71, 72, where β is between about 40° and 85°, preferably between 55° and 80°, and most preferably between 60° and 75°.

Preferably, a thin spacer 81 is used to support the peripheral rims of the diamond windows thereby ensuring the desired height (equal to the optical path length, e.g. 37–50 µm) of the inner measurement chamber 80 of the cuvette, when the two steel members are assembled. The spacer 81 can be a thin circular disc having a circular opening forming the measurement chamber 80, two slots 89, connecting the chamber 80 to the thin bore holes 84, and a pair of guide holes 87' for guide pins 87, used to help positioning the spacer 81 when the cuvette is assembled. The bore holes 85, 86 appearing in the sectional view of FIG. 7 are used for mounting the cuvette on holding means (not shown). The item 82 is an O-ring ensuring that no milk can intrude in the interface between the two cuvette parts.

In the preferred embodiment of the cuvette structure the bore holes 74 and openings 75, 77 are stepped, having stepwise or gradually decreasing diameters, in order to accomodate the inlet and outlet of liquid and IR light to the small measurement chamber 80 in the center of the cuvette.

Even in the enlarged scale view of FIGS. 5A, 5B, 6A, 6B and 7 the measurement chamber 80 containing the milk sample to be measured is hardly visible. The measurement chamber can be, e.g. about 2–3 mm in diameter and about 30–50 µm in width (equal to the optical path length). The actual dimensions in a cuvette in an apparatus according to the invention may depend on the milk or food product to be measured and the parameters wanted.

Figure 9:
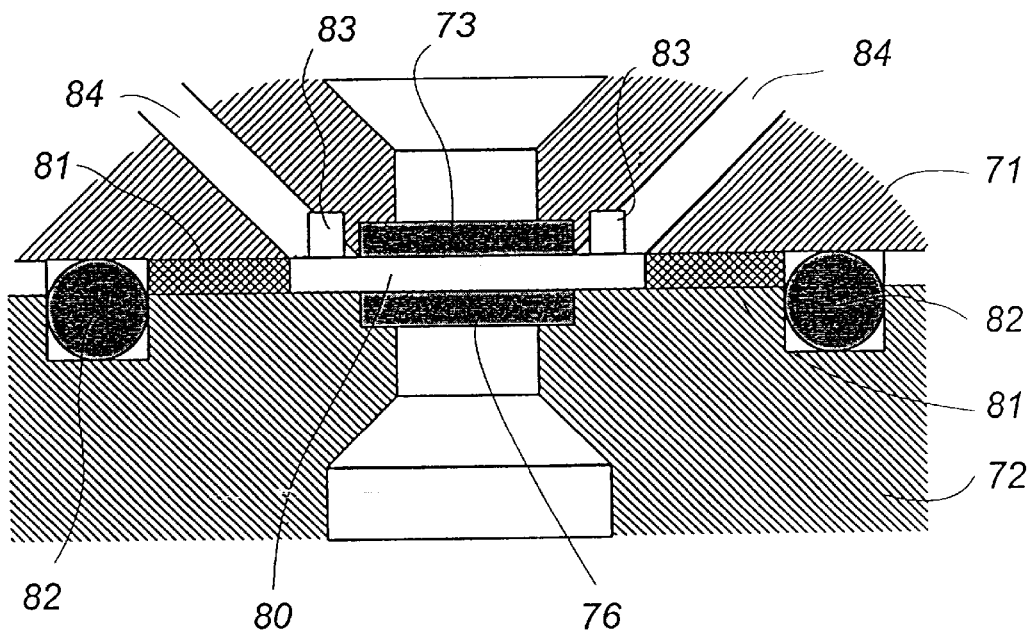
FIG. 9 a sectional elevation of a centre portion of the cuvette including the inner cuvette space in a further enlarged scale, FIG. 10 a vertical projection of the centre portion of FIG. 9, and FIG.
Figure 10:
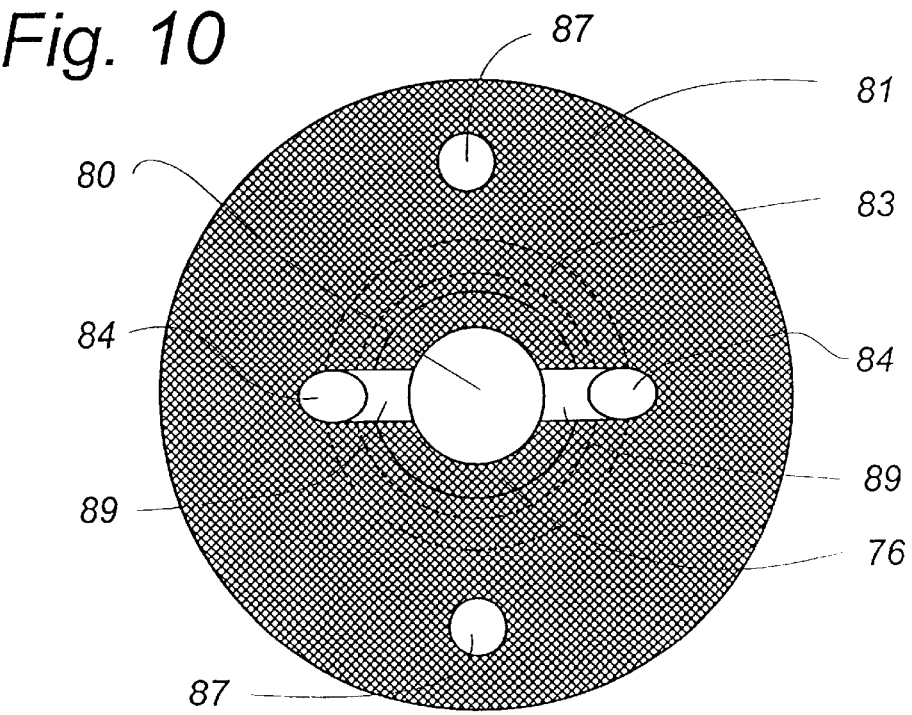

FIG. 9 shows a section through the centre of the cuvette further enlarged in a large scale view, in order to show the inner details of a presently preferred embodiment. Milk flowing through the measuring branch enters the cuvette 70 through the tiny tube 78 at the bore 74 (FIG. 5A) passing the adjacent bore 84 (FIG. 5A and FIG. 9), flows through the slot 89 into the measurement chamber 80 and exits from the cuvette through the opposite slot 89 and the bores 84, 74. Inside the cuvette this flow is forced into a thin (e.g. 30–50 pm thick) and relatively wide (e.g. 0.5–2 mm) flow passing the thin circular measurement chamber 80 between the diamond windows 73, 76. An optional bypass flow path 83 may be provided along the periphery of the windows 73, 76. If the track 83 is provided, preferably it can be restricted and possibly obstructed in order to ensure the measurement chamber is flushed thoroughly with the liquid to be measured. FIG. 10 shows the spacer 81 and the adjacent track 83 and inlet and outlet bores 84. However in the presently preferred embodiment the cuvette has no bypass track 83.

However, the use of diamond windows may cause a serious problem. Due to the dielectic properties of diamond strong internal reflections of the IR-light beam may occur inside the cuvette. Such reflections will strongly influence the obtained spectrometric measurements and should preferably be avoided. Therefore, in an advantageous embodiment the spacer has a wedge form, i.e. having slightly inclined surfaces, providing a difference in light path of from 3 to 10 µm, preferably from 4 to 8 µm and most preferred about 6 µm, across the window opening for the IR light, thereby providing a light path varying e.g. from about 34 to 40 µm across the 2 mm opening. By this feature internal reflections may be eliminated or at least reduced. For sake of simplicity the wedge form is not illustrated in the drawings.

The Control System

As it will be well known to people in the art such an optical system is delicate and has to be kept very stable, in temperature, as well as humidity and protected against vibrations. Therefore a control system 300, preferably including a computer, e.g. a PC with adequate software, monitors and adjusts the temperature at the cuvette. Preferably, the humidity of the optical system 200 is monitored, and connected to an visual or audial alarm function to inform attendant personal that the system need attention, e.g. purging by a suitable gas in order to remove any humidity, as water vapour in the optical path will cause a deterioration of the measurements. Typically means for removing humidity can be included in the optical system. Further, the control system is connected to the pump 40 and valves 23, 45 for control of their operation. The above mentioned monitoring and controlling connections are indicated by dotted and dashed lines 301–305 in FIG. 1. The control system is not shown in details. It may be realized in several known ways. Preferably, the temperature control means comprise a sensor located at a copper member enclosing the cuvette and a heat resistor able to heat the copper member in order to temperature stabilise the cuvette.

The Best Way for Carrying out the method according to the invention.

When the pump 40 is of a type using several pump strokes to provide a sample the method according to the invention is carried out as follows: During a first step of a few seconds duration, e.g. two seconds, the pump 40 is activated by the control means 300. A milk sample is extracted from the process conduit 10 through the fast loop 12 towards the measuring system by the pump. During a second step the milk sample (eg. 1.5 ml milk) is temperature stabilised (heated or cooled) by the means 30. The milk sample stays in the preheater 30 for a period of time, e.g. 25 sec's to attain a predetermined temperature, e.g. 50° C. which is suitable for the homogenizer 50.

During the following third step the pump starts working again, providing a high pressure pushing the heated milk sample through the homogenizer, in which the fat globules of the milk are crunched. From the homogenizer the milk sample flows through the further preheater 60 located upstream the IR cuvette to ensure the sample has the correct temperature for the measurement in the IR cuvette 70.

In the embodiment shown in FIG. 2 the pump is active for about two seconds and preferably less to displace about 1.5 ml through a thin steel tube preferably having a diameter of less than 1 mm$^\varnothing$ e.g. 0.7 mm, connected to the inlet of the cuvette and through the cuvette, through a further thin steel tube connected to the outlet of the cuvette, to the back pressure valve 88 and out of the measuring branch, either to a waste outlet or returned to the fast loop. The major part of the 1.5 ml is flushed through the cuvette with a high flow rate. Assuming a spacer thickness of 50 µm, the sectional area of the cuvette inlet i.e. the slot 89 is 0.050 mm×0.7 mm=0.035 mm². When the 1.5 ml are forced through the cuvette inlet in a short period of preferably less then 2 seconds, the flow rate will exceed, e.g. 45000 mm/2sec=22.5 m/sec. in the inlet 89 to the chamber 80. Thereby, the incoming jet will flush the chamber cleaning IL By adapting. e.g. rounding the transition from the slots 89 to the chamber 80 a laminar flow may be promoted. In the opposite way a sharp transition as shown in FIG. 10 may promote a tubulent flow, which is believed to have a cleaning effect on the cuvette windows. The steel tube leading to the cuvette has an inner area of about 0.4 mm² providing a flow rate of about 1.9 m/s.

When the pump stops, a fraction of the new preheated sample is present in the cuvette. The pressure inside the cuvette will stay at a constant level, of about 10–20 bars preferably 12 bar, due to the back pressure valve 88. Preferably, the following step is about 25 sec's long. In this step the sample is analysed by the IR-spectrometer. In a further step a new sample is extracted from the fast loop. Preferably, the new sample is heated during the following about 25 sec's long step while a portion of the already heated (preceding) sample is measured in the cuvette. And so on. Accordingly, a new sample can be introduced approximately every 30 seconds, corresponding to about 120 measurements per hour.

By the embodiment shown in FIG.3 the pump 40 is a single stroke pump surrounded by heating means, e.g. a coil. The method is carried out as follows: In a first step of about two sec's a sample is sucked into the pump cylinder by one suction stroke of the piston. Then in a second step the sample is heated inside the pump cylinder for about 25 secs. In a third preferably short step of about 0.5–1.0 sec. duration the piston stroke is reversed, pushing the new sample through the homogenizer and partly through the cuvette and the back pressure valve. Thereby the old sample is flushed away either into a waste outlet 90 or returned into the fast loop and the process conduit If the third step is performed in 0.5 sec. the flushing rate through the cuvette will be about 10–30 m/s with a displaced milk volume of about 1.5 ml. This flushing rate will ensure a thorough cleaning of the cuvette windows between each measurement. The advantage of the third embodiment is that the suction stroke may be slow (to avoid cavitation) and the reverse pumping stroke can be fast, thereby providing a high flushing rate and a better cleaning of the cuvette. Also in this embodiment a measurement rate of about 120 samples per hour is possible.

Due to the very stable and wear resistant properties of the cuvette calibrations and zero adjustments will normally only be necessary in the very first upstart of the equipment. However a routine check of the performance of the equipment may be carried out as follows. The measurement apparatus can be checked either
1) by application of a known calibration sample. The known sample is entered in the measurement branch by separating the flexible hose from the sample inlet at the fast loop and by dipping the flexible hose into a cup (110 in FIG.: 2–3) filled with the known sample. A measuring cycle is executed and the result is noted and compared to the known sample data; and/or
2) by taking out a sample from the process stream at a point close to the measuring branch, e.g. at the fast-loop, possibly by separating the flexible hose from the pump 40, and collecting a sample in a cup, (110 in FIG. 2–3), bringing the sample to a reference instrument, e.g. a MilkoScan 50, 120 or system 4000 from Foss Electric A/S, and measuring the sample on the reference instrument.
3) by taking out a number (at least one) samples from the flow of already measured samples leaving the waste outlet 90 in FIG. 1, bringing the sample to a reference instrument, e.g. a MilkoScan 50, 120 or system 4000 from Foss Electric A/S, and measuring the sample on the reference instrument. In order be able to compare the measured waste milk results to the test results from the cuvette the last mentioned procedure has to be carried out in a period of stable production, wherein the samples do not vary noticeably.

Figure 11:
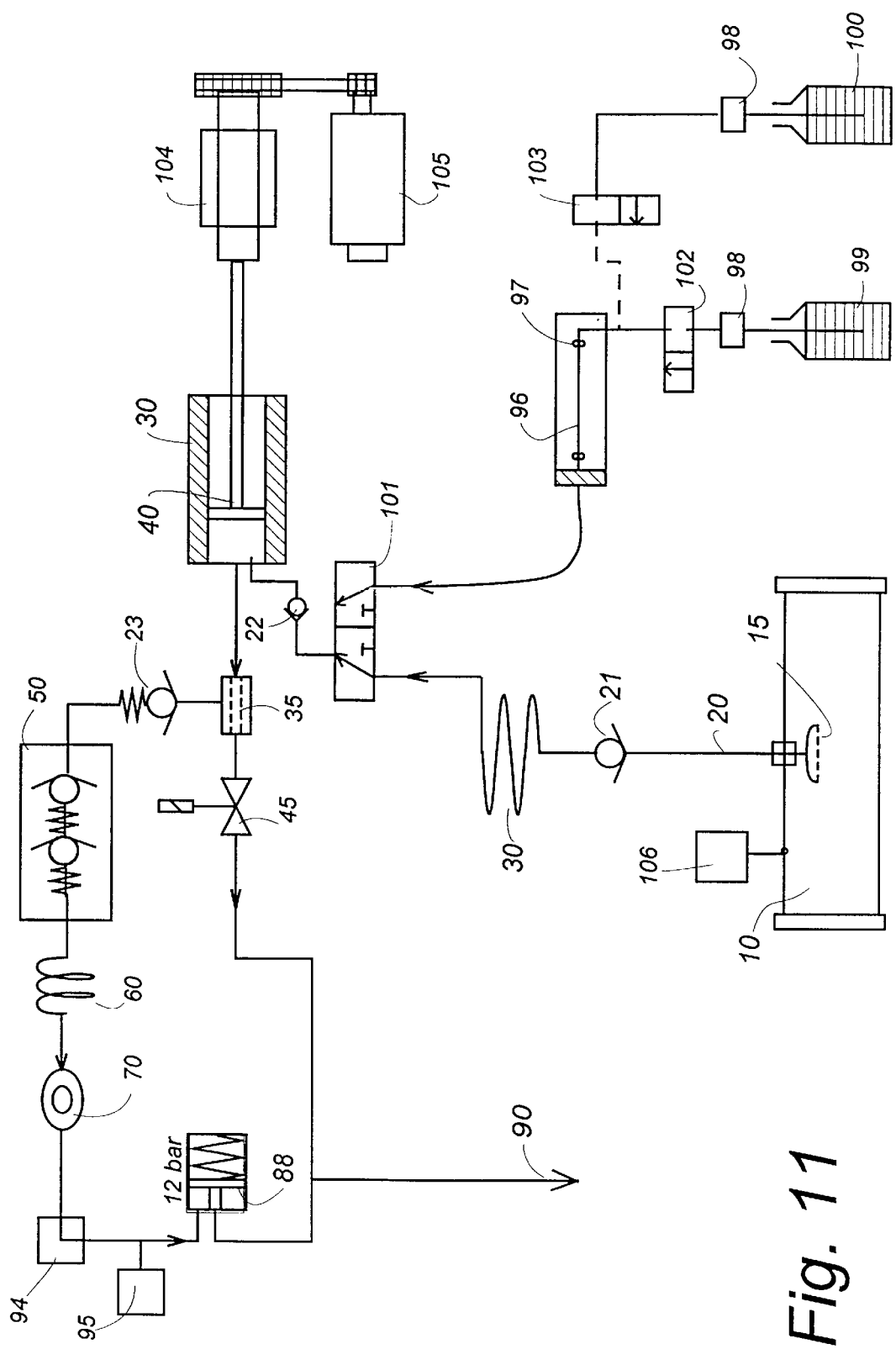
FIG. 11 is a schematic diagram of a further example of a flow system according to the present invention.

In a presently preferred embodiment shown in FIG. 11 a pressure transducer 95 and optionally a flow meter 94 is included, preferably between the cuvette 70 and the back pressure valve 88. The pressure transducer provides a monitoring of the flow system. It will reveal any leakage in the flow system during the measurement During the measurement stable conditions are essential to ensure reproducibility of the measurements. A further advantage is that by measuring the pressure increase (and optionally the flow rate) during flushing the pressure transducer (and optionally the flow meter) provides means for indicating whether the flushing of the cuvette has been sufficient.

Further the preferred embodiment includes an optional arrangement for the intake of a pilot sample in order to monitor the performance of the instrument. A pipette 96 can be arranged to aspirate a pilot sample from a cup (which is not shown). Such a pilot sample has a known specific composition, providing a specific measurement result. In case the actually obtained result differs from the expected values, this indicates that the instrument needs adjustment To ensure a thorough cleaning of the pilot sample pipette the pipette 96 is arranged to be placed in a holder 97 through which it is included in the flow path from a rinsing/cleaning liquid reservoir 100 to the pump 40 when it is not in use for aspiration of a pilot sample.

The provision of the reservoirs 99, 100 for rinsing/cleaning liquid and zero liquid provides for the possibility to arrange a fast cleaning of the cuvette 70 whenever needed. In a presently preferred embodiment a regular cleaning every two hours is recommended. Preferably the liquids are preheated in heaters 98 to the same temperature as the milk samples before entering the measuring branch and the cuvette. Thereby the cleaning can be carried out fast as the heating step (about 25 sec) in the single stroke pump 40 can be dispensed with. I advantageous way the sample pipette 96 is applied for introducing the rinsing/cleaning liquid from the rinsing/cleaning liquid reservoir 100 and/or a zero liquid from a zero liquid reservoir 99. In FIG. 11 the intake is shown through a valve 101 (e.g. a 3/2 way valve) located after (downstream) the sample heater/cooler 30, but the intake may also be located before (upstream) the heater/cooler. Two 2/2 way valves 102, 103 are provided adjacent to the heaters 98 for control of the supply of zero liquid and rinsing/cleaning liquid. Also shown in FIG. 11 is a linear actuator 104 and a motor 105 for driving the single stroke pump 40, 106 indicate an in-line monitoring of the temperature in the process line 10. All components in FIG. 11 having reference numbers used in the previous FIGS. 1–3 are similar to and act the same way as already described with reference to said Figures.

In all the described embodiments of the flow system according to the invention the flow system, i.e. the measuring branch, is capable to withstand standard cleaning procedures for milk plants. Slow build up of deposits on the IR windows of the cuvette is avoided by exposing the cuvette to the standard cleaning procedures of the plant. This may be a so-called "CIP" ("Clean In Place") procedure that uses heated acid and base solutions During cleaning the typical flow rate will be below 10 m/s in the conduits of the milk plant but much higher in the cuvette In an specifically advantageous embodiment of the present invention a number of the cleaning or rinsing liquids of the dairy are used as a calibration liquid for an adjustment or calibration of the optical part and specifically for an adjustment of the calculation and calibration software used for the calculation of the amounts of the tested components. A spectrum measured on a liquid containing. e.g. $NO_3$-ions and/or $PO_4^{3-}$-ions, may be used for an adjustment or calibration of the frequency/wavelength-axe.

As it appears from the foregoing pages a new reliable measurement method, flow system and cuvette has been provided, allowing almost continuous measurements on-line and in-line in diaries with the capacity of about 120 measurements pr. hour. It is obvious to people in the art that the different embodiments of the invention as described in the specification and shown in the drawings may be modified in several ways within the scope of the invention and accordingly the scope of protection is defined by the patent claims.

What is claimed is:

1. A method for carrying out spectrometry for analysis of a liquid food product, possibly containing dissolved gases, in a process line in a liquid food processing plant, and comprising the following steps:

providing a liquid sample from the process line to a measuring branch, thermostating the liquid sample, passing the thermostated liquid food sample into a measurement cuvette, measuring at least a portion of the absorbance spectrum of the liquid food sample in the measurement cuvette, characterised in that the method further comprises extracting the liquid food sample directly from the process line into the measuring branch, providing and maintaining a pressure that is at least as high as the pressure in the said process line, before each measurement flushing the cuvette with a portion of the extracted liquid food sample, the flushing being performed under a pressure of from 50–200 bars across the cuvette, and further having provided that the cuvette has windows of a pressure and wear resistant material.

2. A method according to claim 1, characterised in that a regular cleaning of the measuring branch including the cuvette is performed when the dairy plant is subjected to the regular cleaning process.

3. A method according to claim 2, characterised in that at least one of the cleaning/rinsing solutions in the measuring branch is applied for a standardization and/or adjustment based on characteristics in the measured spectrum or spectra of the cleaning/rinsing solutions especially characteristics originating from the appearance of ions belonging to the group comprising $NO_3$-ions and $PO_4^{3-}$.

4. A method according to claim 1, characterised in that a regular cleaning of the measuring branch including the cuvette is performed by flushing the measurement branch with the same cleaning solutions used for cleaning the dairy plant.

5. A method according to claim 1, characterised in that a regular cleaning of the measuring branch including the cuvette is performed by flushing the measurement branch with a preheated cleaning liquid provided from a reservoir arranged to be connected in fluid communication with the measuring branch.

6. A method according to claim 5, characterised in that at least one of the cleaning/rinsing solutions in the measuring branch is applied for a standardization and/or adjustment based on characteristics in the measured spectrum or spectra of the cleaning/rinsing solutions especially characteristics originating from the appearance of ions belonging to the group comprising $NO_3$-ions and $PO_4^{3-}$.

7. A method according to claim 1, characterised in that the spectrometry is performed in the IR spectral range, preferably in the MID-IR and/or the NIR spectral range.

8. A method according to claim 1, characterised in that the liquid food sample is thermostated while it is maintained inside the cylinder of a single stroke pump.

9. A flow system for in-line extraction of a sample stream from a liquid food processing plant, such as a dairy processing milk and milk products, and for carrying out the method according to claim 1, characterised in the flow system being directly connected to the liquid food processing plant, the flow system including a measurement cuvette for spectrometric measurements for analysis of a liquid food product in the liquid food processing plant, the flow system further comprising pump means and back pressure valve means to maintain a predetermined pressure inside the cuvette, said pressure being at least as high as the pressure inside the process line, and the pump means being able to provide a flushing being performed under a pressure of from 50–200 bars across the cuvette, and the cuvette having windows of a pressure resistant material.

10. A flow system according to claim 9, characterised in that the measurement cuvette has diamond windows.

11. A flow system according to claim 9, characterised in that the pump means is able to induce a liquid by a flow rate of at least 10 m/s into the cuvette for a short period of at least 0.5 sec. said cuvette having a through flow area which is less than 0.5 $mm^2$.

12. A flow system according to claim 9, characterised in that the pump means is a single stroke pump.

13. A flow system according to claim 12, characterised in that the cylinder of the single stroke pump is provided with thermostating means.

14. A flow system according to claim 9, characterised in that the measuring branch of the flowsystem comprises a homogenizer located upstream the cuvette, and at least one preheater located upstream the homogenizer.

15. A flow system according to claim 9, characterised in that the measuring branch of the flowsystem comprises a homogenizer located upstream the cuvette, and at least one preheater located upstream the cuvette.

16. A flow system according to claims 15, characterized in that the preheater is a through flow heater/cooler and that the measuring branch of the flow system comprises an in-line filter located downstream the preheater and the pump and upstream the homogenizer and the cuvette.

17. A flow system according to claim 9, characterised in that the measuring branch of the flowsystem comprises a fast loop for in-line extraction of the liquid food sample from the process tube of the liquid food process plant, and that the measuring branch of the flow system comprises an in-line filter on the fast loop.

18. A flow system according to claims 14, characterized in that the preheater is a through flow heater/cooler and that the measuring branch of the flow system comprises an in-line filter located downstream the preheater and the pump and upstream the homogenizer and the cuvette.

19. A flow system according to claim 9, characterised in that the measuring ranch of the flow system comprises a safety vane located upstream the homogenizer and the cuvette said safety valve further being able to open under the control of control means.

20. A flow system according to claim 9, characterised in that a pilot sample pipette is provided, said pipette being in connectable to the intake of the pump through valve means.

21. A flow system according to claim 20, characterised in that a holder is provided for the pilot sample pipette to be arranged in the holder when it is not immersed in a pilot sample cup, and that the pilot sample pipette when located in the holder is included in a fluid path from a reservoir for a rinsing/cleaning liquid.

22. A flow system according to claim 20, characterised in that a holder is provided for the pilot sample pipette to be arranged in the holder when it is not immersed in a pilot sample cup, and that the pilot sample pipette when located in the holder is included in a fluid path from a reservoir for a zeroliquid through valve means.

23. Cuvette according to claim 22, characterised in that the spacer is made of steel.

24. A measurement cuvette for a flow system according to claim 9, the cuvette comprising: a first and a second steel member, enclosing an IR measurement chamber between two IR windows characterised by the first steel member having bore holes for inlet and outlet of a liquid flow to and from the IR measurement chamber, one of the members having an opening for arrangement of an optical detector, the other member having an opening provided for an IR light beam coming from an IR-source, each opening being sealingly dosed by a diamond disc, forming one of the windows, a metal spacer being arranged between the diamond windows and along the periphery of the measurement chamber, and the two steel members with diamond windows and spacer being tightly secured to each other by fastening means.

25. Cuvette according to claim 24, characterised in that at least one of the bore holes is inclined, forming an angle $\alpha$ with the interface between the two steel members, and $\alpha$ being between 0° and 30°.

26. Cuvette according to claim 24, characterised in that the adjacent bore is inclined, forming an angle $\beta$ with the interface between the two steel members, and $\beta$ being between 40° and 85°.

27. Cuvette according to claim 24, characterised in that a bypass flow path is provided along the periphery of the measurement chamber.

28. Cuvette according to claim 27, characterised in that the spacer has wedge form, i.e. having slightly inclined surfaces, providing a difference in light path of from 3 to 10 $\mu$m across the window opening for the IR light.

29. Cuvette according to claim 27, characterised in that the spacer is provided with slots for the flow of liquid to and from the measurement chamber between the diamond windows in the centre of the cuvette.

30. Cuvette according to claim 24, characterised in that a bypass flow path is provided along the periphery of the diamond windows or the spacer.

31. Cuvette according to claim 24, characterised in that an O-ring is arranged along the periphery of the spacer, outside the spacer.

32. Cuvette according to claim 24, characterised in that an O-ring is arranged along the outer periphery of the bypass flow path.

33. Cuvette according to claim 24, characterised in that at least one of the bore holes is stepped, i.e. having stepwise decreasing diameter from the outside towards the centre of the cuvette.

* * * * *

UNITED STATES PATENT AND TRADEMARK OFFICE
CERTIFICATE OF CORRECTION

PATENT NO.      : 6,297,505 B1
DATED           : October 2, 2001
INVENTOR(S)     : Andreas Skaerlund Frandsen et al.

It is certified that error appears in the above-identified patent and that said Letters Patent is hereby corrected as shown below:

<u>Column 4,</u>
Line 23, delete "spacer_being tightly".
Please delete lines 24-26 entirely.
Line 27, delete "calibrations and adjustments can be dispensed with."

<u>Column 11,</u>
Line 13, change "tubulent" to -- turbulent --.

<u>Column 15,</u>
Line 5, change "ranch" to -- branch --.
Line 16, change "vane" to -- valve --.
Line 10, after "being", delete "in".

<u>Column 16,</u>
Line 8, after "that" delete "at".

Signed and Sealed this

Twenty-fourth Day of June, 2003

JAMES E. ROGAN
*Director of the United States Patent and Trademark Office*